United States Patent  
Liao et al.

(10) Patent No.: US 10,392,631 B2
(45) Date of Patent: Aug. 27, 2019

(54) FUSARIUM CHITIN SYNTHASE GENE CHS3B AND THE USE THEREOF

(71) Applicant: Huazhong Agricultural University, Wuhan (CN)

(72) Inventors: Yucai Liao, Wuhan (CN); Heping Li, Wuhan (CN); Jingbo Zhang, Wuhan (CN); Tao Huang, Wuhan (CN); Xiushi Song, Wuhan (CN); Wei Cheng, Wuhan (CN); Peng Yang, Wuhan (CN)

(73) Assignee: Huazhong Agricultural University, Wuhan (CN)

( * ) Notice: Subject to any disclaimer, the term of this patent is extended or adjusted under 35 U.S.C. 154(b) by 118 days.

(21) Appl. No.: 15/315,124

(22) PCT Filed: Mar. 24, 2015

(86) PCT No.: PCT/CN2015/074994
§ 371 (c)(1),
(2) Date: Nov. 30, 2016

(87) PCT Pub. No.: WO2015/180525
PCT Pub. Date: Dec. 3, 2015

(65) Prior Publication Data
US 2017/0314040 A1    Nov. 2, 2017

(30) Foreign Application Priority Data
May 30, 2014  (CN) .......................... 2014 1 0240032

(51) Int. Cl.
*C12N 15/82* (2006.01)
*C12N 15/80* (2006.01)
*C12N 15/113* (2010.01)
*C12N 9/10* (2006.01)

(52) U.S. Cl.
CPC ....... *C12N 15/8282* (2013.01); *C12N 9/1051* (2013.01); *C12N 15/1137* (2013.01); *C12N 15/80* (2013.01); *C12N 15/8218* (2013.01); *C12Y 204/01* (2013.01); *C12Y 204/01016* (2013.01); *C12N 2310/111* (2013.01); *C12N 2310/14* (2013.01); *C12N 2310/531* (2013.01); *C12N 2330/51* (2013.01)

(58) Field of Classification Search
CPC ......................... C12N 9/1051; C12N 15/8282
See application file for complete search history.

(56) References Cited

PUBLICATIONS

GenBank: JF912410.1 (available online Feb. 17, 2012) (Year: 2012).*
Hannon (Nature (2002) vol. 418) (Year: 2002).*
Kim et al (Curr Genet. Aug. 2009;55(4):449-59) (Year: 2009).*
Koch et al (PNAS Nov. 2013, 110 (48) 19324-19329) (Year: 2013).*
Kong et al (PLoS Pathogens. 2012;8(2):e1002526) (Year: 2012).*
"International Application No. PCT/CN2015/074994, International Search Report dated Jul. 3, 2015", w/ English Translation, (Jul. 3, 2015), 7 pgs.
"International Application No. PCT/CN2015/074994, Written Opinion dated Jul. 3, 2015", (Jul. 3, 2015), 3 pgs.
Martín-Udíroz, Magdalena, et al., "Role of chitin synthase genes in Fusarium oxysporum.", Microbiology 150.10, (2004), 3175-3187.
Popolo, Laura, et al. "Increase in chitin as an essential response to defects in assembly of cell wall polymers in the ggp1delta mutant of *Saccharomyces cerevisiae*", Journal of bacteriology 179.2, (1997), 463-469.
Ueno, Keigo, et al., "Differential cell wall remodeling of two chitin synthase deletants ?chs3A and ?chs3B in the pathogenic yeast Candida glabrata", FEMS yeast research 11.5, (2011), 398-407.

* cited by examiner

*Primary Examiner* — Lee A Visone
(74) *Attorney, Agent, or Firm* — Schwegman Lundberg & Woessner, P.A.

(57) ABSTRACT

The present invention discloses RNAi constructs derived from a *Fusarium* chitin synthase gene Chs3b, which has a nucleotide sequence as shown by SEQ ID NO: 1. Five distinct RNAi vectors are constructed for 5 different segments of the Chs3b gene (named Chs3b-1, 2, 3, 4, and 5, respectively), and separately transformed into *Fusarium*. It is found that siRiNAs in the transformed *Fusarium* shows a significant inhibition in fungal growth, development, and pathogenicity. The expression of the RNAi vectors against Chs3b in plants may inhibit the infection of *Fusarium* and improve the resistance of the transgenic plants to *Fusarium* head blight.

10 Claims, 5 Drawing Sheets
Specification includes a Sequence Listing.

FUSARIUM CHITIN SYNTHASE GENE CHS3B AND THE USE THEREOF

PRIORITY APPLICATIONS

This application is a U.S. National Stage Filing under 35 U.S.C. 371 from International Application No. PCT/CN2015/074994, filed on 24 Mar. 2015, and published as WO2015/180525 on 3 Dec. 2015, which claims the benefit of priority to Chinese Application No. 201410240032.9, filed on 30 May 2014; which applications and publication are incorporated herein by reference in their entirety.

TECHNICAL FIELD

The present invention relates to the field of genetic engineering, and specifically relates to RNAi constructs (vectors) targeting a *Fusarium* chitin synthase gene Chs3b, a method for preparing an RNAi vector of the *Fusarium* chitin synthase gene Chs3b, and the use of the RNAi constructs targeting *Fusarium* chitin synthase gene Chs3b in providing a plant with a disease-resistance trait.

BACKGROUND

Chitin is the main component of the cell wall of fungi, plays a key role in the shaping of fungal cells, and is required for maintaining the integrity of the structure of cell wall and the growth and development of the cells. Chitin is a linear chain-like polymer formed by connecting N-acetyl-glucosamine via β-1,4-glycosidic bond and is catalytically synthesized by chitin synthase (Chs). Chitin synthase is a membrane-binding protein, which catalyses the transfer of N-acetyl-D-glucosamine from UDP-N-acetyl-D-glucosamine to a growing chain of chitin for continuous synthesis of chitin. Inactivation of the chitin synthase gene may result in a disorder of the structure of cell wall, deformed fungal cell, unstable osmotic pressure, and an increased sensitivity to the change of osmotic pressure outside (Specht et al., The chsD and chsE genes of *Aspergillus nidulans* and their roles in chitinsynthesis. Fungal Genet Biol. 1996. 20: 153-167).

The number of the chitin synthase genes varies in different fungi. An ancient fungus, *Encephalitozon cuniculi*, has only one chitin synthase gene, while *Rhizopus oryzae* has more than 20 chitin synthase genes (Latgé et al., The cell wall: a carbohydrate armour for the fungal cell. Mol Microbiol. 2007. 66: 279-290). The chitin synthase genes play different functional roles even in the same fungi. For example, the genome of *Fusarium oxysporum* contains 6 chitin synthase genes (Martín-Urdíroz et al., a class VII chitin synthase involved in septation, is critical for pathogenicity in *Fusarium oxysporum*. Eukaryot Cell. 2008. 7: 112-121). Inactivation of Chs1 gene resulted in no significant change in the phenotype and pathogenicity of the mutant strain, but resulted in a much higher average number of nucleoli per cell than that of WT, and a reduced content of chitin in the mutant by 10%. Inactivation of Chs2 and Chs7 genes resulted in a decreased pathogenicity, with no significant change to the number of nucleoli per cell. Inactivation of Chs2 gene further resulted in 10% decrease in the level of chitin (Martín-Urdíroz et al., Role of chitinsynthase genes in *Fusarium oxysporum*. Microbiology. 2004. 150: 3175-3187). No mutant with an inactivated Chs3 gene was obtained, which suggested that the inactivation of this gene has a lethal effect. Inactivation of ChsV gene would result in a dramatic decrease in the pathogenicity of the mutant strain which lost its ability to infect a plant, had severely damaged integrity of cell wall, and was very sensitive to fungicides (Madrid et al, Class V chitinsynthase determines pathogenesis in the vascular wilt fungus *Fusarium oxysporum* and mediates resistance to plant defense compounds. Mol Microbiol. 2003. 47: 257-266). Inactivation of ChsVb gene resulted in a more significant change in the phenotype of the mutant strain which had an abnormal septum, and balloon-like structures appeared in different parts of hyphae. In the mutant strain, a special phenomenon, called intrahyphal hyphae, could be observed by TEM. The mutant strain totally lost its pathogenicity, and was very sensitive to fungicides. As can be seen, ChsV and ChsVb genes play an important role in maintaining the integrity of the cell wall of *Fusarium oxysporum* and in infecting plants (Martín-Urdíroz et al., a class VII chitin synthase involved in septation, is critical for pathogenicity in *Fusarium oxysporum*. Eukaryot Cell. 2008. 7: 112-121). A Chs1 gene was cloned and separated from *Fusarium graminearum* (Li et al., Cloning and characterization of a gene coding for a class I chitin synthase from *Fusarium graminearum*. Can. J. Plant Pathol. 2003. 25: 240-248). It was found that a significant change in the structure of the cell wall of a ΔChs1 mutant strain obtained by homologous knockout occurred. The activity of the chitin synthase, the level of chitin, the number of conidia, the length of large conidia, and the pathogenicity for wheat of the ΔChs1 mutant strain significantly decreased as compared to WT (Xu et al., Disruption of the chitin synthase gene Chs1 from *Fusarium asiaticum* results in an altered structure of cell walls and reduced virulence. Fungal Genet Biol. 2010. 47 (3): 205-215).

As chitin is an important functional component of fungal cell wall, and only specifically appears in fungal cell wall and the shell of crustaceans, insects and other arthropods, but not in plants and mammals, chitin and chitin synthase become ideal targets for developing new fungicides and controlling fungus diseases (Bowman and Free et al., The structure and synthesis of the fungal cell wall. BioEssays. 2006.28: 799-808; Latgé et al., The cell wall: a carbohydrate armour for the fungal cell. Mol Microbiol. 2007. 66: 279-290).

In recent years, the use of host-induced gene silencing (RIGS) technology in controlling plant diseases provides a new approach to the control of plant diseases. RNAi vectors against target genes which are important for the growth, development, and pathogenicity of pathogens were expressed in host plants such that, when the plants were invaded by the pathogens, the expression of the endogenous target genes in the fungi would be interfered with the corresponding dsRNA/siRNA, which resulted in the inhibition of the invasion of the pathogens (Nowara et al., RIGS: host-induced gene silencing in the obligate biotrophic fungal pathogen *Blumeria graminis*. The Plant Cell. 2010. 22: 3130-3141; Koch et al., Host-induced gene silencing of cytochrome P450 lanosterol C14α-demethylase-encoding genes confers strong resistance to *Fusarium* species. Proc Natl Acad Sci USA. 2013. 110 (48): 19324-19329). The choice of target genes is crucial for the effect of HIGS. Genes which can be used as the target of RIGS include key genes for growth and development and lethal genes, crucial genes for pathogenicity, and genes required for the invasion of pathogens. Once RNAi vectors constructed with the sequences of these target genes are introduced into a host plant, the expression of the target genes of the pathogens will be silenced by the host through an RNAi pathway, and thus the disease are controlled. With targeting specificity based on nucleotide sequence, this technology enables the generation of stable environment-friendly transgenic plants, and exhibits potential in application.

SUMMARY OF THE INVENTION

An objective of the present invention is to provide a *Fusarium* chitin synthase gene Chs3b as an ideal target for developing new fungicide and controlling fungal diseases, and provide a new genetic resource for improving disease-resistance trait of plants.

Another objective of the present invention is to provide a method for preparing RNAi vectors of the *Fusarium* chitin synthase gene Chs3b, wherein respective segments of the target gene are used for the preparation of the RNAi vectors for the screening of effective RNAi interfering segments.

Another objective of the present invention is to provide the use of antisense or hairpin loop structures from the *Fusarium* chitin synthase gene Chs3b in providing a plant with a disease-resistance trait. The expression of RNAi vectors targeting Chs3b gene in plants enables the generation of new genetically stable environment-friendly transgenic plants, and exhibits potential in application.

When antisense or hairpin loop RNA structures derived from Chs3b gene of the present invention or the DNA fragment thereof is constructed into a fungus or plant expression vector, any of strong promoters, specific promoters, inducible promoters, and other regulation sequences suitable for fungi or plants can be added before the transcription initiation of the gene for ensuring the transcription of the target sequence.

According to the present invention, Chs3h gene or its homologs can be used as targets for developing new fungicide and controlling fungal diseases for other different kinds of pathogenic fungi.

Any segments of Chs3b gene of the present invention or its homologs can be used as a HIGS target for designing RNAi vectors based on a hairpin loop structure or expressing dsRNA/siRNA. The vectors can be introduced into host plants such as wheat and barley by using biotechnologies such as gene gun, agrobacterium, plant viral vectors, and microinjection for silencing the expression of Chs3b gene or its homologs in corresponding pathogens through RNAi pathway, so as to control diseases and obtain a disease-resistance trait.

The present invention has achieved the above objectives by following:

A method for cloning *Fusarium* chitin synthase gene Chs3b, comprising the steps of:

1) extracting total RNA from the hyphae of *Fusarium graminearum* 5035 having grown on PDA medium for 3 days by using Trizol extraction kit;

2) synthesizing a first strand cDNA: degrading genomic DNA in the total RNA by using DNase I (RNase free), followed by synthesizing the first strand cDNA by using the first strand cDNA synthesis kit (SuperScript™ III Reverse Transcriptase Kit);

3) amplifying full-length Chs3b cDNA by PCR by using the following primers designed in accordance with the cDNA sequence of Chs3b (FGSG_10116) gene in the *Fusarium* Comparative Database:

```
                                            (SEQ ID NO: 17)
Chs3bcdnaclonePl :ATGGCGTACAATGGCCGTGAC (SEQ ID NO: 18)
Chs3bcdnacloneP2 :TTAATTTCTTGAGAAACAG
``` and, isolating and obtaining the cDNA sequence of Chs3b gene, an isolated gene having a nucleotide sequence of SEQ ID NO. 1 (2718 bp in length).

A method for preparing RNAi vectors of *Fusarium* chitin synthase gene Chs3b, comprising the following steps:

Chitin synthase gene Chs3b was isolated and cloned from *Fusarium graminearum* 5035 strain (a *Fusarium graminearum* strain having high pathogenicity, which was isolated and preserved by the applicant's lab in Wu Han, in 1999). No mutant with Chs3 gene knock-out was obtained, which suggested that this gene is a lethal gene closely relating to the growth and development of *Fusarium graminearum*. For 5 different segments of Chs3b gene (named, Chs3b-1, Chs3b-2, Chs3b-3, Chs3b-4 and Chs3b-5, respectively), 5 different fungal RNAi vectors having a hairpin loop structure (named, pChs3bRNAi-1, pChs3bRNAi-2, pChs3bRNAi-3, pChs3bRNAi-4 and pChs3bRNAi-5, respectively) were constructed. The nucleotide sequence (SEQ ID NO.1) contains the sequence information of the fungal transformation vectors, pChs3bRNAi-1, pChs3bRNAi-2, pChs3bRNAi-3, pChs3bRNAi-4, and pChs3bRNAi-5. These pChs3bRNAi vector were separately introduced into wildtype *Fusarium graminearum* 5035 strains by protoplast transformation, and specifically incorporated into PLS gene site, resulting in five Chs3bRNAi strains. Inhibited growth and development, reduced chitin content (by 5.3-33% for Chs3bRNAi-2, Chs3bRNAi-3, and Chs3bRNAi-5 strains), and reduced pathogenicity (by 22-47% at seedling stage and by 64-72% at flowering stage, for Chs3bRNAi-1, Chs3bRNAi-2, Chs3bRNAi-3 and Chs3bRNAi-5 strains) of these strains as compared to those of wild-type 5035 strains were observed. The results showed that Segment 1, Segment 3 and Segment 5 are most effective RNAi interfering segments, followed by Segment 2, with Segment 4 not very effective.

Use of hairpin loop structures derived from *Fusarium* chitin synthase gene Chs3b in providing a plant with a disease-resistance trait, comprising the following steps:

Hairpin loop RNAi constructs of Chs3b-1, Chs3b-3, and Chs3b-5, demonstrated to have the most significant RNAi interfering effect on *Fusarium*, were separately used to construct plant RNAi vectors, pXJC-Chs3bRNAi-1, pXJC-Chs3bRNAi-3 and pXJC-Chs3bRNAi-5. The nucleotide sequence (SEQ ID NO.1) contains the sequence information of the plant transformation vectors, pXJC-Chs3bRNAi-1, pXJC-Chs3bRNAi-3, and pXJC-Chs3bRNAi-5. The vectors were co-transformed into wheat by gene gun method to obtain transgenic wheat plants which may produce corresponding siRNAs. The expression of invading *Fusarium* Chs3b gene was silenced by RNAi, and thus the invasion of the pathogens was inhibited. Challenging with *Fusarium* at seedling stage and at flowering stage showed that, the resistance of the transgenic wheat plants thus obtained to *Fusarium* head blight (FHB) was significantly improved. The incidence of the disease for the transgenic wheat plants decreased by 75-89% at seedling stage and by 56-70% at flowering stage after being challenged with *Fusarium* as compared to that of non-transgenic control plant Yangmai 15.

The plants suitable for the present invention include economic and food crops, such as wheat, barley, corn, rice, and rapeseed. According to the present invention, Chs3b or its homologs can be used as target genes for controlling other different types of fungal diseases such as wheat (barley) powdery mildew, wheat (barley) rust, rice blast, wheat (corn, rice) sheath blight and for improving the disease-resistance trait of economic crops such as wheat, barley, corn, and rice.

In an embodiment of present invention, a RNAi construct targeting a *Fusarium* chitin synthase gene Chs3b having a nucleotide sequence of SEQ ID NO, 1, a fragment or homologue thereof is provided.

In a preferred embodiment of the RNAi construct, the RNAi construct is designed based on a hairpin loop structure and/or to form a dsRNA/siRNA or antisense sequence directed to the *Fusarium* chitin synthase gene Chs3b, a fragment or homologue thereof.

In a more preferred embodiment of the RNAi construct, the RNAi construct is directed to a fragment of *Fusarium* chitin synthase gene Chs3b selected from the group consisting of: Chs3b-1 having a nucleotide sequence of SEQ ID NO. 2, Chs3b-2 having a nucleotide sequence of SEQ ID NO, 3, Chs3b-3 having a nucleotide sequence of SEQ ID NO, 4, Chs3b-4 having a nucleotide sequence of SEQ ID NO. 5, and Chs3b-5 having a nucleotide sequence of SEQ ID NO. 6.

In another preferred embodiment of the RNAi construct, it is a fungical transformation vector preferably selected from the group consisting of: pChs3bRNAi-1, pChs3bRNAi-2, pChs3bRNAi-3, pChs3bRNAi-4 and pChs3bRNAi-5.

In another preferred embodiment of the RNAi construct, it is a plant transformation vector, and preferably the hairpin loop structure sequence therein is modulated by a constitutive promoter (e.g., a corn Ubi promoter) and terminated by Nos terminator, and more preferably it is selected from the group consisting of: pXJC-Chs3bRNAi-1, pXJC-Chs3bRNAi-2, pXJC-Chs3bRNAi-3, pXJC-Chs3bRNAi-4 or pXJC-Chs3bRNAi-5.

The present invention also provides a transfected cell comprising the RNAi construct according to present invention, wherein the cell is a bacterial cell (preferably fungal cell), an animal cell or a plant cell.

The present invention also provides a method for producing a plant resistant to *Fusarium* head blight, comprising the steps of transforming the plant with the RNAi construct according to claim 1, and expressing the RNAi construct to form/express a dsRNA/siRNA or antisense sequence directed to the *Fusarium* chitin synthase gene Chs3b, a fragment or homologue thereof.

In a preferred embodiment of the method of present invention, the plant is selected from the group consisting of wheat, barley, corn, rice, rapeseed and oat.

The present invention also provides a plant resistant to *Fusarium* head blight produced by the method of present invention. In particular, the plant is preferably selected from the group consisting of wheat, barley, corn, rice, rapeseed and oat.

THE DESCRIPTION OF FIGURES

A: The phenotypes of wild-type strain 5035 and respective Chs3bRNAi strains cultured in a PDA medium or in a PDA medium supplemented with various stressing agents for 3 days. B: left: the pathogenicity analysis of wild-type strain 5035 and respective Chs3bRNAi strains introduced into wheat strain Annong 8455 at seedling stage; right: the pathogenicity analysis of wild-type strain 5035 and respective Chs3bRNAi strains introduced into wheat strain Sumai No. 3 at flowering stage ($P<0.05$).

Figure 3:
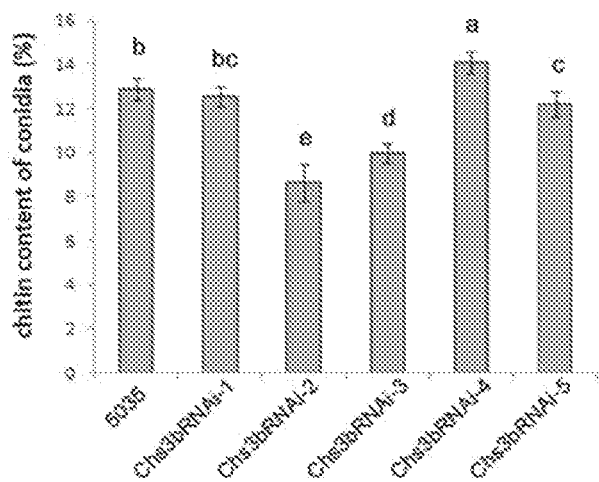

FIG. 3 shows the chitin content measurement of wild-type strain. 5035 and respective Chs3bRNAi strains ($P<0.01$).

Figure 4:
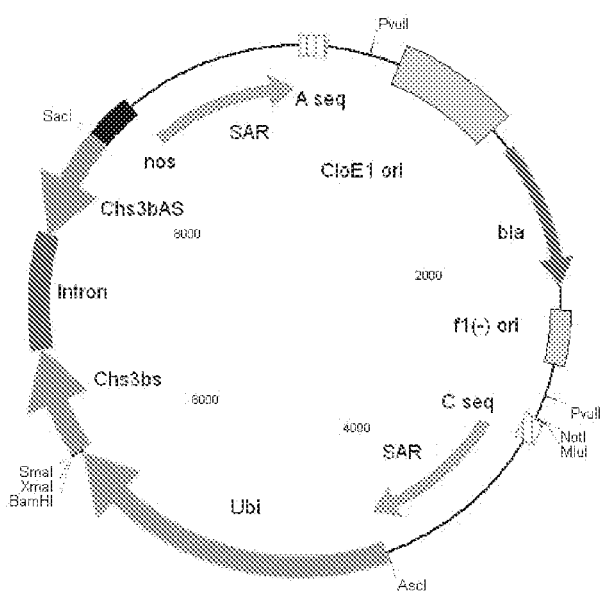

FIG. 4 is a schematic view of a plant pXJC-Chs3bRNAi expression vector.

Figure 5:
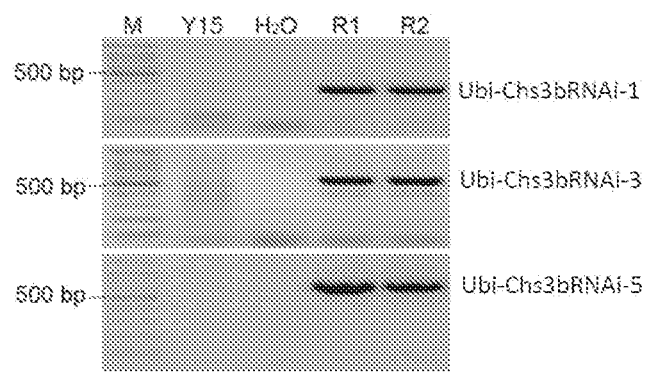

FIG. 5 shows the results of the PCR assay performed on transgenic Chs3bRNAi wheat plants $T_5$). Y15: negative control plant; $H_2O$: blank control plant; R1 and R2: two transgenic Chs3bRNAi-positive plants, respectively.

Figure 6:
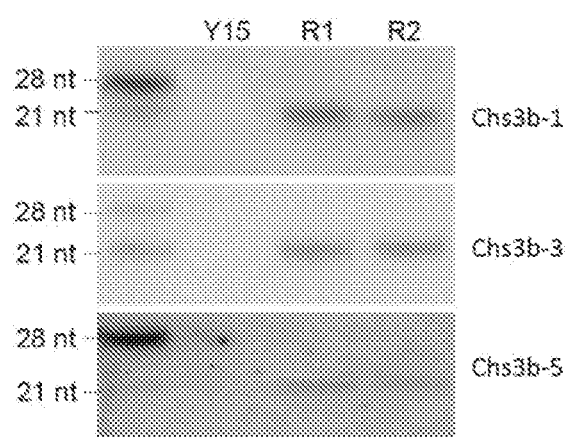

FIG. 6 shows the results of siRNA Northern blotting assay of transgenic Chs3bRNAi wheat plants ($T_5$). Y15: negative control plant; R1 and R2: two is different transgenic Chs3bRNAi-positive plants, respectively.

Figure 7:
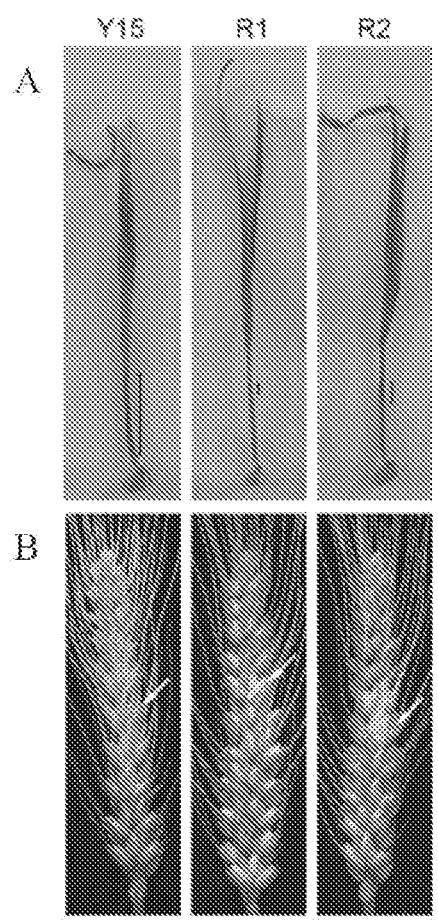

FIG. 7 shows the morbidity of transgenic Chs3bRNAi wheat plants ($T_5$) challenged with *Fusarium*. Y15: negative control plant; R1 and R2: two different transgenic Chs3bRNAi-positive plants, respectively, After challenged with *Fusarium* at seedling stage (A), the plaque length is 1.45 cm for the non-transgenic control plants, while it is 0.16 cm for the transgenic plant. R1 and 0.36 cm for the transgenic plant R2. Morbidity was reduced by 75-89%. After challenged with *Fusarium* at flowering stage (B), the spikelet illness rate for the non-transgenic control plants is 36.9%, while is 11.1% for the transgenic plant R1 and 16.3% for the transgenic plant R2. Morbidity was reduced by 56-70%. The resistance of the transgenic wheat plants to *Fusarium* head blight was improved significantly ($P<0.01$.).

EMBODIMENTS

Example 1

The Isolation and Cloning of cDNA of Chs3b Gene

Chs3b gene of the present invention corresponds to the sequence of FGSG_10116 disclosed in *Fusarium* Comparative Database (http://www.broadinstitute.org/annotation/genome/fusarium_graminearum/Multi Home.html). cDNA sequence was amplified from the hyphae of *Fusarium graminearum* 5035 cultured on PDA medium for 3 days by routine RT-PCR. method (see, "Molecular Cloning: A Laboratory Manual $3^{rd}$ Edition", Joseph Sambrook and David W Russell, translated by HUANG Peitang and WANG Jiaxi, Science Press, 2002).

A method for cloning *Fusarium* chitin synthase gene Chs3b according to the present invention, comprising the steps of:

1) RNA was extracted from the hyphae of *Fusarium graminearum* 5035 (a *Fusarium graminearum* strain having high pathogenicity, which was isolated and preserved by the applicant's lab in Wu Han, in 1999) cultured on PDA medium for 3 days by using Trizol extraction kit (Invitrogen) according to the manufacturer's instructions.

2) Synthesis of first strand cDNA: (1) Genomic DNA mixed in the total RNA was degraded with DNase I (RNase free). A 50 µl reaction system was prepared: 10×DNase I Buffer 5 µl, DNaseI (RNase free) 2 µl, RNase inhibitor (40 U/µl) 0.5 µl, total RNA 3 µg, ddH$_2$O (RNase free) q.s. to 50 µl. After reaction at 37° C. for 40 min, 150 µl of ddH$_2$O (RNase free) was supplemented; then, 200 µl of P.C.I. was added and mixed thoroughly; centrifugation was performed at 4° C., 12000 r/min for 15 min; 180 µl of upper liquid was transferred to a new centrifuge tube, to which an equal volume of C.I. was then added and mixed thoroughly; centrifugation was performed at 4° C., 12000 r/min for 10 min; 160 µl of upper liquid was transferred to a new centrifuge tube, to which 160 µl of isopropanol was then added and mixed thoroughly, left at room temperature for 15 min; centrifugation was performed at 4° C., 12000 r/min for 15 min; the supernatant was removed, and then the precipitant was washed with 500 µl of 75% (v/v) ethanol solution pre-cooled at 4° C.; centrifugation was performed at 12000 r/min for 15 min; the supernatant was removed, and the precipitant was left at room temperature and allowed to be dried; 20 µl of ddH₂O (RNase free) was added to dissolve RNA; and 1 µl of the solution was sampled for electrophoresis. (2) RNA of high quality thus obtained was subjected to following reaction using first strand cDNA synthesis kit (SuperScript™ III Reverse Transcriptase Kit) according to the manufacturer's instructions: Oligo (dT)20 (100 ng/µl) 3 µl, dNTPs (10 mmol/L) 1 µl, and RNA 2 µg were mixed; to the mixture, ddH₂O (RNase free) was added to 13 µl; reaction was performed at 65° C. in water bath for 5 min, followed immediately by ice bathing for 3 min; after short centrifugation for seconds, 5× First-stand Buffer 4 µl, DTT (0.1 mol/L) 1 µl, RNase inhibitor (40 U/µl) 0.5 µl, SuperScript™ III Reverse Transcriptase (200 U/µl) 0.5 µl, and ddH2O (RNase free) 1 µl were added and gently mixed; the reaction mixture was incubated at 50° C. for 60 min, then heated to 70° C. for 15 min to inactivate the enzyme, and then cooled in ice bath for 3 min; and stored at −20° C. for use.

3) Full-length Chs3b cDNA was amplified by PCR using the following primers designed in accordance with the cDNA sequence of Chs3b (FGSG_10116) gene in the *Fusarium* Comparative Database:

```
                                           (SEQ ID NO: 17)
Chs3bcdnacloneP1:ATGGCGTACAATGGCCGTGAC (SEQ ID NO: 18)
Chs3bcdnacloneP2:TTAATTTCTTGAGAAACAG.
```

PCR reaction system (total 50 µl): cDNA first strand template 1 µl, 10×LA PCR buffer 5 µl, 10 mM dNTP 4 µl, each of forward and reverse primers 1 µl, LATaq enzyme 0.5 µl, water added q.s. to 50 µl (the agents used in the PCR reaction can be purchased from Takara Bio., Da Lian). PCR reaction conditions: pre-denaturing at 95° C. for 3 min; 95° C. 20 s, 54° C. 30 s, 72° C. 2.5 min, for 35 cycles; extending at 72° C. For 10 min, and 4° C. for storage.

4) The product of the PCR reaction was ligated to T/A cloning vector pMD18-T (Takara Bio., Da Lian) and sequenced by using primers M13F and M13R (provided together with pMD18-T) for verification. The cDNA sequence of Chs3b gene, as an isolated gene, was thus obtained. An isolated gene having a nucleotide sequence of SEQ ID NO. 1 (2718 bp in length). An isolated protein having an amino acid sequence of SEQ ID NO. 2 (905 amino acids).

Figure 1:
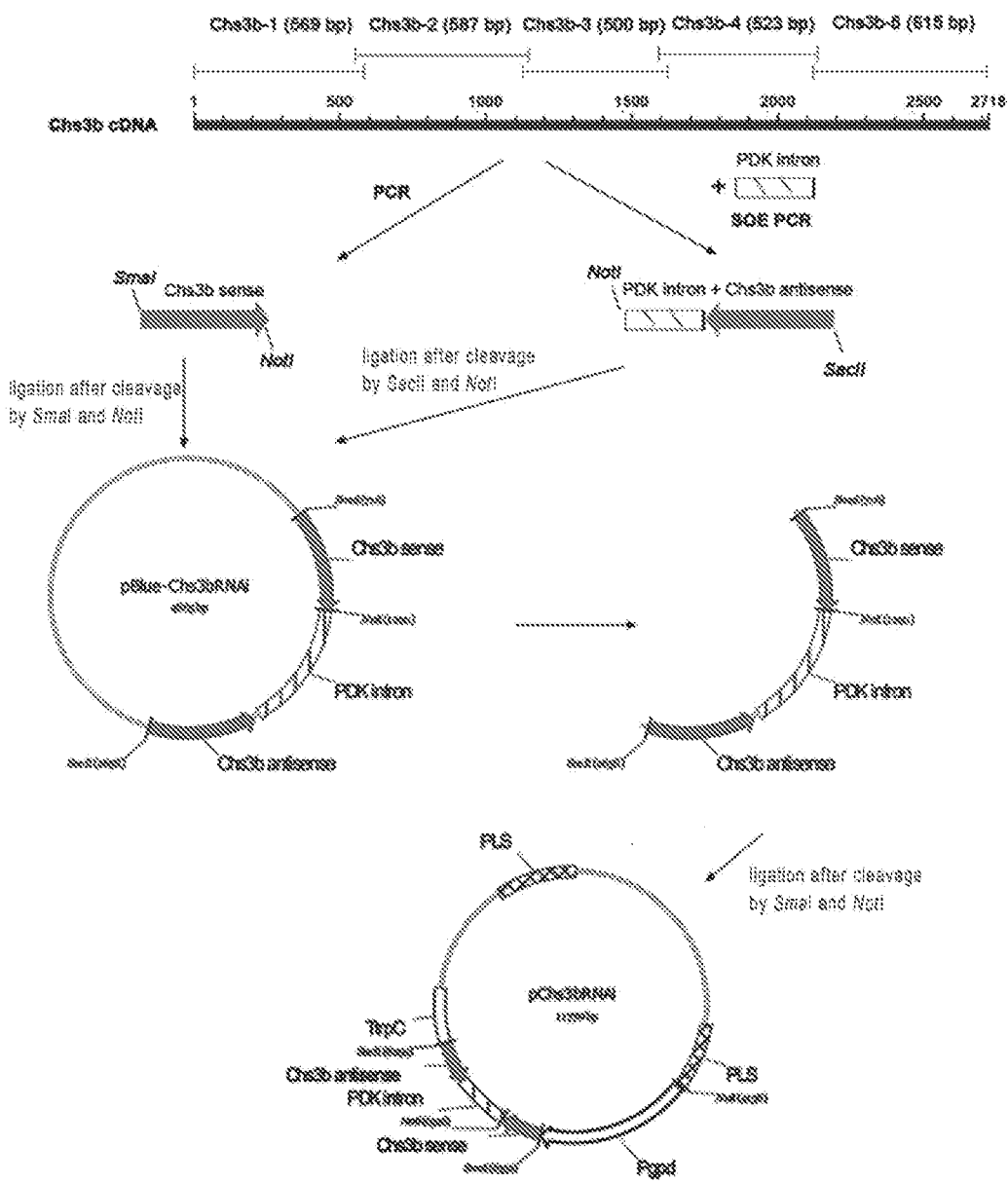
FIG. 1 is a schematic view showing the division of Chs3b gene into 5 segments and the construction of corresponding fungal pChs3bRNAi vectors.

Example 2: Construction of RNAi Vectors Against Respective Segments of Chs3b Gene and the Transformation into Fungi 1) According to the present invention, Chs3b gene was divided into 5 segments (FIG. 1), named, respectively, Chs3b-1, Chs3b-2, Chs3b-3, Chs3b-4, and Chs3b-5 (569 bp, 587 bp, 500 bp, 523 bp, and 615 bp in size, respectively). The neighboring two have an overlap of about 14 bp.

Forward sequences of each of these segments was amplified by using the following specific PCR primers:

```
Chs3bRNAi1s-P1:
                                           (SEQ ID NO: 7)
TCCCCCGGGTCTTGAGGGTGAAGTCGTTGGGAT

Chs3bRNAi1s-P2:
                                           (SEQ ID NO: 8)
ATAAGAATGCGGCCGCCCGTGACCAGGAGTATGGAGGC

Chs3bRNAi2s-P1:
                                           (SEQ ID NO: 9)
TCCCCCGGGTGTAGAAACCCTCCCAAAGAGCAAG

Chs3bRNAi2s-P2:
                                           (SEQ ID NO: 10)
ATAAGAATGCGGCCGCCTTCACCCTCAAGAACGGTTACGA

Chs3bRNAi3s-P1:
                                           (SEQ ID NO: 11)
TCCCCCGGGCAGAGTGGCAGCGAACGAACC

Chs3bRNAi3s-P2:
                                           (SEQ ID NO: 12)
ATAAGAATGCGGCCGCTCCTTGCTCTTTGGGAGGGTTTC

Chs3bRNAi4s-P1:
                                           (SEQ ID NO: 13)
TCCCCCGGGTAATAAGAGCGACCAGAATAACACCACCAG

Chs3bRNAi4s-P2:
                                           (SEQ ID NO: 14)
ATAAGAATGCGGCCGCTCGTTCGCTGCCACTCTGTACTCGCTGATG

Chs3bRNAi5s-P1:
                                           (SEQ ID NO: 15)
TCCCCCGGGCCTGCCGAGGAACCACAAGAAACC

Chs3bRNAi5s-P2:
                                           (SEQ ID NO: 16)
ATAAGAATGCGGCCGCGCTGGTGGTGTTATTCTGGTCGCTCTT
```

PCR reaction system (total 50 µl): cDNA first strand template 1 µl, 10× LA PCR buffer 5 µl, 10 mM dNTP 4 µl, each of forward and reverse primers 1 µl, LATaq enzyme 0.5 µl, water q.s. to 50 µl (the agents used in the PCR reaction can be purchased from Takara Bio., Da Lian). PCR reaction condition: pre-denaturing at 95° C. for 3 min; 95° C. 20 s, 56° C. 30 s, 72° C. 30 s, for 35 cycles; extending at 72° C. for 10 ruin. The product of the PCR reaction recovered from gel was subjected to cleavage of restrict enzymes SmaI and NotI and then ligated into pBlueScript SK (+) vector, resulting in pBlue-Chs3b vectors carrying respective forward segments.

PDK intron+reverse sequence of each of respective segments of Chs3b was amplified by using the following SOE-PCR primers:

```
PDK-P1:
                                           (SEQ ID NO: 19)
ATAAGAATGCGGCCGCGCTTGGTAAGGAAATAATTA

Chs3bRNAi1as-P2:
                                           (SEQ ID NO: 20)
TTCCCCGCGGGGATCGAGCTCTCTTGAGGGTGAAGTCGTTG

Chs3bRNAi2as-P2:
                                           (SEQ ID NO: 21)
TTCCCCGCGGGGATCGAGCTCTGTAGAAACCCTCCCAAAGAGCAAG

Chs3bRNAi3as-P2:
                                           (SEQ ID NO: 22)
TTCCCCGCGGGGATCGAGCTCCAGAGTGGCAGCGAACGAACC

Chs3bRNAi4as-P2:
                                           (SEQ ID NO: 23)
TTCCCCGCGGGGTTCGAGCTCTAATAAGAGCGACCAGAATAACACC
```

-continued

Chs3bRNAi5as-P2:
(SEQ ID NO: 24)
TGCTCCGCGGCGATCGAGCTTTAATTTCTTGAGAAACAGCACATG.

SOE-PCR reaction system (total 50 µl): 10×LA PCR buffer 5 µl, 10 mM dNTP 4 µl, each of forward and reverse primers 1 µl, LATaq enzyme 0.5 µl, water q.s. to 48 µl; 95° C. 3 min; 95° C. 10 s, 56° C. 30 s, 72° C. 40 s, for 7 cycles; adding PDK intron and each of the reverse segments of Chs3b at a molar ratio of 1:1; 95° C. 10 s, 56° C. 30 s, 72° C. 40 s, for 35 cycles; extending at 72° C. for 10 min. The product of the PCR reaction recovered from gel was subjected to cleavage of restrict enzymes NotI and SacII and then ligated into the pBlue-Chs3b vectors carrying the forward segments, resulting in a pBlue-Chs3bRNAi vector carrying each of the segments. Then, Chs3b sense-PDK intron-Chs3b antisense hairpin loop structure was digested by SmaI and SacII, and then the product of the digestion was ligated into fungal transformation vectors to form pChs3bRNAi vectors carrying each of the segments (pChs3bRNAi-1, pChs3bRNAi-2, pChs3bRNAi-3, pChs3bRNAi-4 and pChs3bRNAi-5, see FIG. 1). The nucleotide sequence (SEQ ID NO.1) contains the sequence information of the fungal transformation vectors, pChs3bRNAi-1, pChs3bRNAi-2, pChs3bRNAi-3, pChs3bRNAi-4 and pChs3bRNAi-5.

2) The five RNAi interference vectors were introduced into the protoplasts of *Fusarium graminearum* 5035 by using fungal protoplast transformation method (Maier et: al., Development of a highly efficient gene targeting system for *Fusarium graminearum* using the disruption of a polyketide synthase gene as a visible marker. FEN/IS Yeast Res. 2005. (5): 653-662). A promoter, Chs3bRNAi hairpin loop structure sequence, and terminator were incorporated into PLS gene site in a site-directed manner, which resulted in *Fusarium graminearum* strains Chs3bRNAi-1, Chs3bRNAi-2, Chs3bRNAi-3, Chs3bRNAi-4, and Chs3bRNAi-5.

Example 3: Screening for Effective RNAi Interfering Segments for *Fusarium graminearum* Chs3b Gene 1. Osmotic Pressure Sensitivity Assay.

Figure 2:
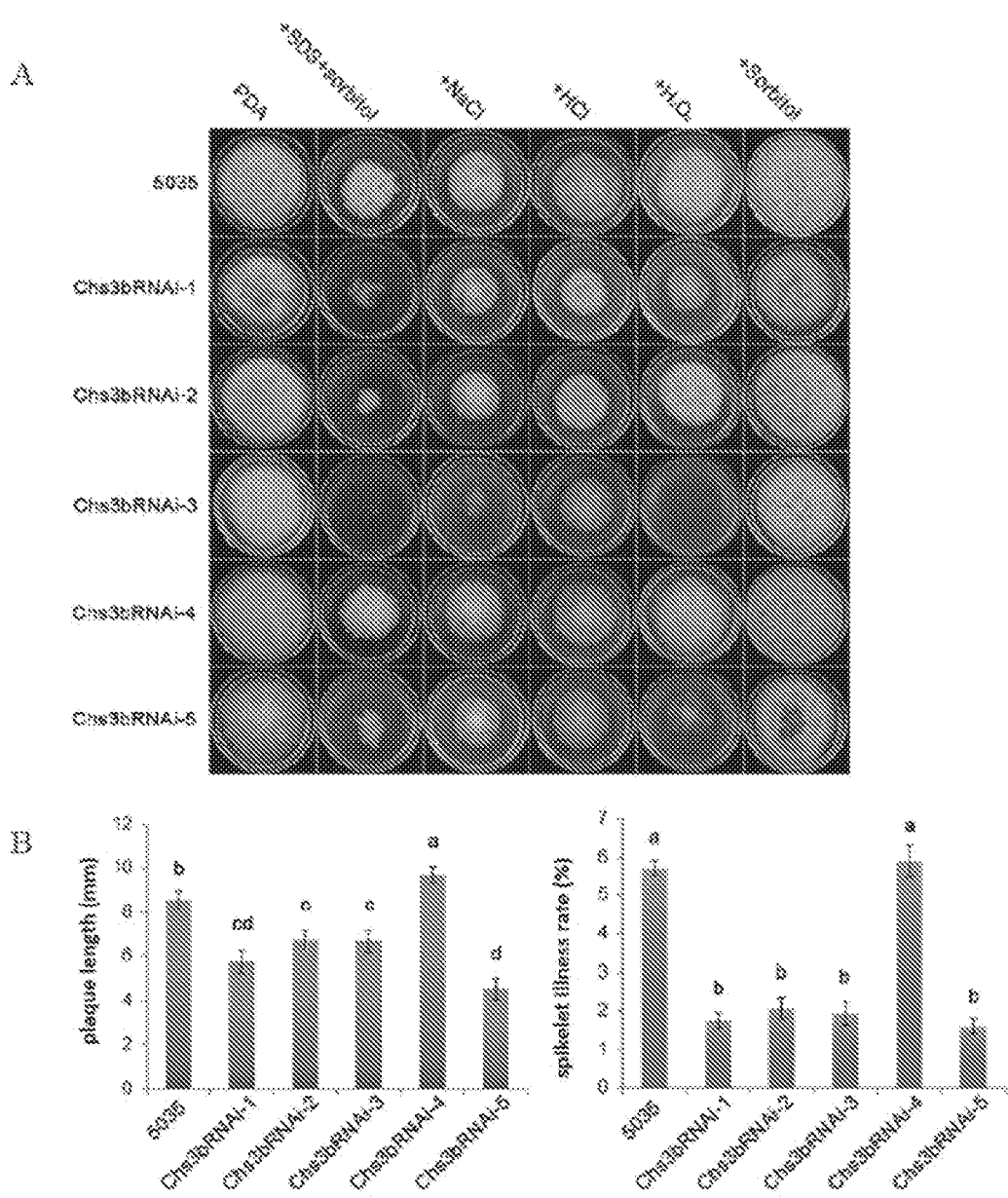
FIG. 2 shows the sensitivity to osmotic pressure and pathogenicity of respective *Fusarium graminearum* Chs3bRNAi strains.

The following medium plates were prepared: FDA (potato 200 g, boiled for 15 min to obtain extract, to which glucose 20 g and agar 15 g were added, followed by distilled water to a total volume of 1000 ml, and sterilized at 121° C. for 20 min); PDA supplemented with 1.2 mol/L sorbitol and 0.025% (w/v) SDS; PDA supplemented with 1.2 mol/L NaCl; PDA supplemented with 6 mmol/L HCl; PDA supplemented with 1.43 mmol/L $H_2O_2$; and, PDA supplemented with 1.2 mol/L sorbitol. 7 ml of each of the media was added into a 6-cm dish. 10 µl of fresh conidium or ascospore liquid of each of the strains having a concentration of $5 \times 10^5$/ml was seeded on the center of the medium plates, which were then placed in an incubator at 28° C. in dark for 3 days. Subsequently, the morphology of the colonies formed was observed. The results showed that: the strains Chs3bRNAi-1, Chs3bRNAi-3, and Chs3bRNAi-5 cultured in a PDA medium or in a PDA medium supplemented with various stressing agents showed the most significant decrease in biomass, followed by Chs3bRNAi-2 strain (FIG. 2A). This demonstrated that, RNAi interference against these four segments of Chs3b gene may result in a decrease in the biomass and growth of the hyphae.

2. Challenging at Seedling Stage and Flowering Stage.

1) Challenging at Seedling Stage.

Mature seeds were sterilized on surface: treated with 70% (vol/vol) ethanol for 30 sec; washed once with sterilized water quickly; sterilized with 0.1% mercuric chloride for 6-8 min; washed with sterilized water for 3-4 times, 2 min each time. After sterilization, the seeds were placed with back up evenly in a plastic box covered with wet filter paper, and incubated at room temperature for 3 days for germination. The tips of the coleoptiles of the simultaneously budding seeds were cut off by 2-3 mm. 3 µL of *Fusarium* 5035 spore suspension ($5 \times 10^5$/mL) was applied at the wound of the coleoptiles, and then incubated at 25° C., 95% relative humidity, with 16 h light on, for 7 days. The plaques on the coleoptiles were photographed and their length was measured.

2) Challenging at Flowering Stage.

10 µL of the suspension of *Fusarium* 5035 spores ($5 \times 10^5$/mL) was injected by a microsyringe between the outer rafter and inner rafter of a floweret outside the middle of the main ears of wheat grown well and uniformly at an early flowering stage, and kept wet at 25° C., 90% relative humidity or above for 3 days. Subsequently, a relative humidity of about 70%-80% was maintained by spraying water three times a day (in the morning, at noon, and in the evening). After 21 days, the number of ill spikelets and the total number of spikelets were investigated, and spikelet illness rate was calculated using the following equation:

$$\text{Spikelet illness rate} = \frac{\text{Number of ill spikelets}}{\text{Total number of spikelets}} \times 100\%$$

The results were analysed for their differentiation by using Student's test and multiple comparison in variance analysis.

The analysis of the pathogenicity at seedling stage and at flowering stage showed that, the pathogenicity of the *Fusarium graminearum* was reduced especially for Segments 1, 2, 3, and 5 of Chs3b gene (reduction by 22-47% at seedling stage, and by 64-72% at flowering stage, FIG. 2B).

3. Measuring Chitin Content

Formulation: 50 mg/ml N-acetylglucosamine: 250 mg of N-acetylglucosamine was dissolved in ultrapure water to a final volume of 5 ml, divided into aliquots and stored at −20° C.; 6 mol/L HCl: ultrapure water was added to 51.72 ml of conc. HCl to a final volume of 100 ml; Solution A (1.5 mol/L $Na_2CO_3$ in 4% (v/v) acetylacetone): $Na_2CO_3$ 15.9 g, 100% (v/v) acetylacetone (Sigma) 4 ml, dissolved in sterilized water to a final volume of 100 ml, and stored at 4° C.; Solution B (1.6 g of 4-dimethylaminobenzaldehyde in 30 ml conc. HCl and 30 ml 95% ethanol): 4-dimethylaminobenzaldehyde 1.6 g, dissolved in 30 ml of 95% ethanol, to which 30 ml of conc. HCl was added and gently stirred, the resulting solution was stored at 4° C.

Spores of each of the strains were collected by centrifugation using centrifuge tubes which had been pre-weighed, and washed twice with sterilized water. Supernatant was removed, and the spores left in the centrifuge tubes were lyophilized. The centrifuge tubes together with the spores therein were weighed, making sure that the net weight of the spores in the centrifuge tubes is 5 mg. 1 ml of 6 mol/L HCl was added to the spores for acidolysis at 100° C. for 17 h. Samples were dried in a vacuum drier at 52° C. to remove HCl. The dried samples were redissolved in 1 ml of sterilized water. After thorough dissolution, centrifugation was performed to remove insoluble substances. To 100 µl of the resulting supernatant, 100 µl of Solution A was added and mixed. Then, the mixture was placed in a water bath and boiled at 100° C. for 20 min. The boiled sample was removed and allowed to cool to room temperature. Then, 700 µl of 95% (vol/vol) ethanol and 100 µl of Solution B were added and mixed thoroughly. The mixture was left at room temperature for 1 h, followed by measuring the OD520 value of the sample. There were 18 replicates for each strain. Chitin content was expressed as the percentage of the weight of the glucosamine released from the acidolysis accounting for the weight of the lyophilized hyphae or spores. The results showed that: chitin content decreased significantly (by 5.3-33%, $P<0.01$) with RNA interference for Segments 1, 2, 3, and 5 of Chs3b gene as compared to wild-type strains (see, FIG. 3).

Example 4: Construction and Genetic Transformation of Plant Chs3bRNAi Expression Vectors 1. Construction of Plant Chs3bRNAi Expression Vectors.

The screening for effective RNAi interfering segments of *Fusarium graminearum* Chs3b gene showed that, the RNAi interfering effect of segments Chs3b-1, Chs3b-3 and Chs3b-5 was most significant. To confirm whether expression of dsRNA/siRNA against this target gene in plants by using HIGS technology can improve the resistance of transgenic wheat plants to *Fusarium* head blight, plant expression vectors of present invention, pXJC-Chs3bRNAi-1, pXJC-Chs3bRNAi-3, and pXJC-Chs3bRNAi-5, were constructed by using the Chs3b-1, Chs3b-3 and Chs3b-5 fragments of Chs3b gene, respectively. Maize polyubiquitin genes: structure, thermal perturbation of expression and transcript splicing, and promoter activity following transfer to protoplasts by electroporation. Plant Mol. Biol. 18, 675-689) (see FIG. 4 for the schematic views of the vectors). The nucleotide sequence (SEQ ID NO.1) contains the sequence information of the plant transformation vectors, pXJC-Chs3bRNAi-1, pXJC-Chs3bRNAi-3 and pXJC-Chs3bRNAi-5. The hairpin loop structure of these 3 vectors is modulated by a constitutive promoter-corn Ubi promoter, and terminated by Nos terminator. The plasmids pXJC-Chs3bRNAi-1 and pXJC-Chs3bRNAi-3 were subjected to cleavage using restriction enzyme MluI, and the plasmid pXJC-Chs3bRNAi-5 was subjected to cleavage using restriction enzyme NotI. After gel electrophoresis, the minimum expression cassette DNA segment (the promoter, the hairpin loop structure, the terminator and protective bases of about 150 bp at two ends) was obtained by gel recovery and used for gene gun bombardment.

2. Wheat Genetic Transformation.

The plant expression vectors pXJC-Chs3bRNAi-1, pXJC-Chs3bRNAi-3, and pXJC-Chs3bRNAi-5 and a screening marker gene, bar, in minimum expression cassette, were co-transformed into a wheat plant "Yangmai 15" by a wheat genetic transformation method using gene gun. Resistant plants were obtained through immature embryo callus induction, gene gun bombardment, recovery culturing, differentiation screening, and rooting, sound seedling cultivation, and transplant. The specific process of the wheat genetic transformation was as follows:

1) Taking Off Immature Embryo and Callus Induction:

The ears of wheat were cut off 12-14 days after flowering, and uniform immature seeds were taken off from the middle part. The seeds were placed in a sterile flask in a laminar flow cabinet. To the seeds, an amount of 70% ethanol was added for sterilization for 30 sec. Then, the seeds were washed once quickly with sterilized water. Then, 0.1% mercuric chloride was added for sterilization for 6-8 min. Then, the seeds were washed with sterilized water for 3-4 times, 2 min for each time. The process was performed with the flask shaked continuously for thorough sterilization. Semi-transparent immature embryos (0.8-1.2 mm) were taked off under a sterile condition. The immature embryos were seeded into induction medium IMI with scutellum upward at 50-60 embryos per dish, and incubated at 27° C. in dark for 4-6 days.

2) Hypertonic Treatment:

Embryogenic calluses in a sound state were selected and transferred into hypertonic medium MSH in a circle having a diameter of about 2 cm. After 4-6 hours of hypertonic treatment, transformation was performed by gene gun bombardment, followed by further hypertonic treatment for 16-20 h and cultivation at 27° C. in dark.

3) Gene Gun Bombardment:

Preparation of vector particles: 50 μL of a prepared suspension of gold powder (50 mg/mL) was dissolved at room temperature, and sonicated for 1 min; gold powder was mixed by vortex, then 5 μL of DNA (3 μg/μL) was added and mixed by vortex; thereafter, 50 μL of 2.5 mol/L $CaCl_2.2H_2O$ (sterilized by suction filtration) and mixed by vortex; 20 μL of 0.1 mol/L spermidine (sterilized by suction filtration) was added slowly dropwise, with centrifuge tubes in continuous vortexing for 3 min; the tubes were then left in ice bath for 1.5 min; supernatant was removed by pipetting; 300 μL of 70% (vol/vol) ethanol was further added to resuspend the precipitant, and the resuspension was then left in ice bath for 15 min; supernatant was removed by pipetting; the precipitant was finally resuspended in 100 μL of absolute ethanol (10 μL/shot), vortexed to homogeneous and then applied onto particle supporting sheet, and air-dried in a laminar flow cabinet for subsequent gene gun bombardment.

Bombardment parameters: pressure: 1100 psi; distance: 9 cm; degree of vacuum: 27.5 inches number of bombardment: 1; the amount of gold powder used for each shot: 250 μg/shot; the amount of DNA used: 1.5 μg/shot.

4) Recovery Culturing:

After bombardment, the calluses were subjected to further hypertonic treatment for 16-20 h, and then transferred to induction medium MS1 for recovery culturing at 27° C. in dark for 2-3 weeks, followed by differentiation screening.

5) Differentiation Screening:

After recovery culturing, the calluses were transferred to differentiation screening medium MSB3 (3 mg/L Bialaphos) for a first run of differentiation screening at 22° C. in light for 16 h. After 2 weeks, the calluses having green spots were transferred to differentiation screening medium. MSB5 (5 mg/L, Bialaphos) for a second run of differentiation screening. Regenerated seedlings (height >2 cm) were transferred to rooting screening medium MST5 (5 mg/L Bialaphos) in a straight tube or a triangle flask for 1-2 runs of further screening (2 weeks for each run).

6) Seedling Cultivation, Vernalization and Transplant:

After rooting screening, robust seedlings were transferred to seedling cultivation medium MST0 (without screening pressure) for 3-4 days and then placed at 4° C. for vernalization for 2 weeks, and then transplanted to green house (20-22° C., 16 h light on) for growing.

See Table 1 for the composition of the media.

TABLE 1

Media used in the wheat genetic transformation

| Medium Type | Composition |
|---|---|
| Induction medium | MS + 0.1 g/L inositol + 0.5 g/L glutamine + 0.1 g/L casein hydrolysate + 30 g/L sucrose + 2 mg/L 2, 4-D + 2.7 g/L phytagel, pH 5.8 |
| Hypertonic medium | Induction medium + 0.2 mol/L mannitol + 0.2 mol/L sorbitol + 2.7 g/L phytagel, pH 5.8 |
| Differentiation screening medium | MS + 0.1 g/L, inositol + 30 g/L sucrose + 5 mg/L ZT + 3-5 mg/L Bialaphos + 2.7 g/L phytagel, pH 5.8 |
| Rooting screening medium | MS (major element reduced to a half level) + 0.1 g/L inositol + 20 g/L sucrose + 0.5 mg/L NAA + 5 mg/L Bialaphos + 2.7 g/L phytagel, pH 5.8 |
| Seedling cultivation medium | MS (major element reduced to a half level) + 0.1 g/L inositol + 20 g/L sucrose + 0.5 mg/L, NAA + 2.7 g/L, phytagel, pH 5.8 |

Example 5: PCR Assay of Chs3bRNAi Transgenic Wheat

To confirm whether the resistant plants thus obtained were positive transgenic plants, 2 stable transgenic plants, named R1 and R2 respectively, were obtained by PCR assay performed on the plants of $T_0$-$T_5$ generation. The results of PCR assay on the plants of $T_5$ are shown in FIG. 5. Specific target bands could be amplified from the transgenic plants R1 and R2, but not from the negative control plant and blank control. In this Example, the PCR assay was performed as follows:

1. Extraction of Genomic DNA from Wheat (CTAB Method):

1) Leaves of wheat at 3-4 leaf stage were placed in a 2-mL centrifuge tube containing a steel ball. After pre-cooling in liquid nitrogen, samples were ground using TissueLyser II (QIAGEN).

2) To the samples, 900 μL of pre-heated CTAB buffer was added and mixed is to homogeneous, and left in water bath at 65° C. for 1 h, with the tubes upside down for 3-4 times.

3) 305 μL of 5 mol/L, KAc and 225 μL of chloroform were added and mixed to homogeneous by upside down until the color of the bottom of the solution turned to dark green, for about 5 min, and left at −20° C. for 30 min.

4) After centrifugation at 12000 r/min. for 15 min, 900 μL, of supernatant was transferred to a new centrifuge tube, to which 900 μL of PCI was added and mixed to homogeneous gently by reversing the tube for 5 min.

5) After centrifugation at 12000 r/min. for 15 min, 800 μL, of supernatant was removed (white particle-like solid of protein at the interface of upper liquid and lower liquid should not be taken). To the supernatant, an equal volume of CI was added and mixed to homogeneous by reversing. Then, centrifugation was performed at 12000 r/min for 15 min to remove the remaining phenol.

6) 700-800 μL, of supernatant was transferred from the centrifuge tube to a new 1.5-mL centrifuge tube, to which 0.8-fold volume of isopropanol and 0.1-fold volume of 3 mol/L NaAc were added and mixed by reversing and left at room temperature for 10 min.

7) After centrifugation at 12000 r/min for 15 supernatant was removed, is and precipitant was washed with 500 μL of pre-cooled 70% (vol/vol) ethanol. After centrifugation at 12000 r/min for 5 min, supernatant was discarded.

8) After air-drying at room temperature, an appropriate volume of TER (TE:RNAase=499:1) was added to dissolve DNA before storage at −20° C. for use.

2. PCR Assay:

Reaction system: 2× Taq PCR Mix 10 μL, 0.5 μL, of 10 μmol/L each of forward and reverse primers (see, Table 2), template DNA 100-150 ng, ddH$_2$O q.s. to 20 μL. Reaction procedure: pre-denaturing at 95° C. for 5 min; denaturing at 94° C. for 40 sec, annealing at 58° C. (annealing temperature depends on the primers employed) for 40 sec, extending at 72° C. for 30 sec (time for extension depends on the length of the fragment to be amplified, extending rate: generally 1 kb/min), for 35 cycles; further extending at 72° C. for 7 min. After PCR reaction, 1.0 μL of PCR product was subjected to electrophoresis (1% (w/v) agarose gel, 90 V, −40 min). The gel was photographed and recorded by using a UV imaging device.

TABLE 2

Primers for PCR amplification

| Primer | Annealing site | Sequence (5'-3') | Size (bp) |
|---|---|---|---|
| ZJB | Ubi promoter | GTTTCTTTTGTCGATGCTC ACCC (SEQ ID NO: 25) | |
| Chs3bR1 | Chs3bRNAi-1 | CCGACTCTGCCTTTGATCC TG (SEQ ID NO: 26) | 333[a] |
| Chs3bR3 | Chs3bRNAi-3 | ATCTTGGTGGTGCTTGTGG T (SEQ ID NO: 27) | 533[b] |
| Chs3bR5 | Chs3bRNAi-5 | GTCGCTCTTATTACCATTT ACG (SEQ ID NO: 28) | 633[c] |

[a]Target fragment (333 bp) of Ubi-Chs3bRNAi-1 for PCR assay was amplified with primers ZJB and Chs3bR1.
[b]Target fragment (533 bp) of Ubi-Chs3bRNAi-3 for PCR assay was amplified with primers ZJB and Chs3 bR3.
[c]Target fragment (633 bp) of Ubi-Chs3bRNAi-5 for PCR assay was amplified with primers ZJB and Chs3bR5.

Example 6: siRNA-Northern Blotting Assay of Chs3bRNAi Transgenic Wheat

To confirm whether siRNA was formed in the Chs3bRNAi transgenic wheat plants, the transgenic plants R1 and R2 as well as the negative control plants were tested by northern blotting (FIG. 6). siRNA interfering molecules of about 21 nt formed in the transgenic plants R1 and R2, but not in the negative control plants. In the Example, si-RNA northern blotting was performed as follows:

1. Extraction of Small RNA from the Transgenic Plants (Purelink™ miRNA Isolation Kit)

1) 0.1 g of leaf tissue of the plant was ground in liquid nitrogen into powder which was then transferred into a 1.5-mL centrifuge tube. Then, 300 μl of L3 was added and vortexed.

2) Centrifugation was performed at room temperature at 12000 rpm for 2 min. Supernatant was transferred into a new centrifuge tube, to which, 300 μl of 70% (v/v) ethanol was added to a final concentration of 35%, with vortexing.

3) The mixture solution was loaded onto a column, and then centrifuged at 12000 rpm for 1 min, with total RNA bound on the column. The liquid in the collective tube was preserved 4) To the collective tube, 96%-100% ethanol was added to a final concentration of 70% (i.e., 700 μL of 96%-100% ethanol was added to 600 μL of the solution), and then vortexed.

5) 700 μL of the vortexed solution was loaded onto a second column, and then centrifuged at 12000 rpm for 1 min, with siRNA/miRNA bound on the column. The waste was discarded. This step may be repeated once.

6) 500 μL of washing solution (W5) was added. Centrifugation was performed at 12000 rpm for 1 min. The waste was discarded. This step may be repeated once.

7) Centrifugation was performed at a maximum rate of 13200 rpm for 2-3 min. Residual washing solution was discarded.

8) The centrifuge column was placed into a 1.5-mL centrifuge tube. 50 μL of DEPC ddH$_2$O (pH>7.0) was added for elution. The eluent was allowed to stand at room temperature for 1. min, centrifuged at a maximum rate for 1 min, and then stored at −80° C. for use.

2. SDS-PAGE:

1) Glass plates, comb, and tank to be used in electrophoresis were first washed with Liquinox washing agent, followed by DEPC H$_2$O containing 10% (w/v) of SDS and then with 95% ethanol in DEPC H$_2$O.

2) The glass plates, comb, and tank were assembled.

3) Electrophoresis buffer 0.5×TBE was prepared with DEPC H$_2$O.

4) 15% polyacrylamide gel (10 mL)

| | |
|---|---|
| 5 × TBE | 1 mL |
| 30% polyacrylamide | 5 mL |
| Urea | 4.2 g |
| DEPC H$_2$O | 0.75 mL |

Urea was completely dissolved at 37° C. or room temperature. Then, 70 μL of 10% (w/v) APS and 3.5 μL of TEMED were added and mixed by reversing but no vortexing. The mixture was immediately poured into the gel plate. The comb was inserted into the plate. Polymerization was carried out for 30 min or more.

5) Electrophoresis was pre-run at 100V for 30 min.

6) To the RNA sample (30 μg), 2×RNA Loading buffer was added and mixed. After short centrifugation, the mixture was heated at 65° C. for 10 min. Thereafter the sample was immediately cooled on ice for 1 min and then loaded. Make sure each sample has an identical volume.

7) Electrophoresis was performed at 100-150V until bromophenol blue (bottom dye) reached the lower quarter of the gel.

3. Blot Transferring (Bio-Rad Semi-Dry)

1) After the electrophoresis, the gel plate was removed and placed in 0.5×TBE to separate gel sheet with its part of loading holes discarded.

2) 2 pieces of extra-thick whatman filter paper and 1 piece of nitrocellulose membrane (Hybond-N$^+$ Amersham) were cut to have an identical size to the gel and soaked in 0.5×TBE for 5-10 min.

3) One filter paper, nitrocellulose membrane, gel, and the other filter paper were aligned from anode to cathode with no bubble therebetween.

4) Transferring was performed at 400 mA for 45 min, and then the device was disassembled.

5) The membrane was dried at room temperature and fixed using UV transmission crosslinking device (1200J× 100) for subsequent hybridization or storage at 4° C.

4. Pre-Hybridization and Hybridization:

1) The membrane was placed in a hybridization tube of an appropriate volume. To the tube, 5 mL of PerfectHyb™ plus buffer was added for pre-hybridization at 38° C. in a hybridization oven for at least 1 h.

2) Preparation of probes: DNA segments were amplified by PCR, electrophoresed, and recovered from gel. Probes were radiolabelled using a random primers labeling kit (Takara). Labeling was performed as follows: to a 1.5-mL centrifuge tube, 150 ng of DNA segment and 2 μL of random primers were added, and then water was added to a volume of 17 μL; the mixture was boiled in boiling water for 5 ruin, then cooled in cold water for 8 min, and then centrifuged; 2.5 μL of 10× Buffer, 2.5 μL of dNTP, 2 μL of α-[$^{32}$P]-dCTP, and 1 μL of DNA polymerase were added and incubated in water bath at 37° C. for 3 h.

3) The labeled probes were boiled in boiling water for 5 min, then cooled in an ice bath for 10 ruin, and then added to a hybridization tube (direct addition on a membrane was not allowed). Hybridization was performed at 38° C. for about 16 h.

5. Membrane Washing and Autoradiograph:

1) Hybridization buffer was poured into a barrel for radioactive waste.

1×SSC and 0.1% SDS were added into the hybridization tube, and rotated gently for washing the membrane for 2-3 times. The hybridized membrane was transferred from the hybridization tube to a tray containing sufficient membrane washing solution (1×SSC and 0.1% SDS). The tray was shaked for 15 min. The second-time membrane washing solution was poured into a barrel for radioactive waste. Sufficient membrane washing solution (0.1×SSC and 0.1% SDS) was added, and shaked at 40° C. for 10-20 min. During washing, the membrane should be kept wet. The radioactivity of the membrane should be monitored through the washing. When radioactivity signal reduced significantly, the washing was stopped.

2) The membrane was removed from the membrane washing solution and placed on clean filter paper. Most of liquid was removed (too dry was not allowed; no visible water spot would just be OK). The membrane was wrapped with a piece of preservative film. When the signal was 20-25 caps, the wrapped membrane was placed in an exposure folder and allowed to contact a phosphor screen with the membrane facing the white side for 3-12 h. Then, the phosphor screen was removed and imaged on a phosphor screen imager. The membrane was then washed with membrane washing solution (0.1×SSC and 0.1% SDS) for each time, and the signal was monitored until it was 8-15 caps. The time for exposure was correspondingly increased to 24-72 h.

Example 7: Identification of the Resistance of Chs3bRNAi Transgenic Wheat Plants to Diseases To determine whether siRNA formed in the Chs3bRNAi transgenic wheat plants can inhibit the growth of invading *Fusarium*, the trait of the transgenic plants resistant to *Fusarium* head blight was confirmed by challenging at seedling stage and at flowering stage (see, Table 3 and FIG. 7). For the details of the process employed in this Example to identify disease-resistant trait, refer to the method used in Example 3 for challenging at seedling stage and at flowering stage. Statistically, in terms of phenotype, the resistance of transgenic plants to *Fusarium* head blight was significantly different from that of non-transgenic control Yangmai 15 (P<0.01). 7 days after challenging with *Fusarium* at seedling stage, the length of the plaques on the non-transgenic control plants was 1.45 cm, while it was 0.16 cm for the transgenic plant R1 and 0.36 cm for the transgenic plant R2, with a reduction of 75% to 89%. 21 days after challenging with *Fusarium* at flowering stage, the spikelet illness rate for the non-transgenic control plants was 36.9%, while it was 11.1% for the transgenic plant R1 and 16.3% for the transgenic plant R2, with a reduction of 56% to 70%.

TABLE 3

Identification of the resistance of the Chs3bRNAi transgenic wheat plants to Fusarium head blight

| Genotype | Plaque length (challenging at seedling stage) (cm) | Spikelet illness rate (challenging at flowering stage) (%) |
|---|---|---|
| R1 | 0.16 ± 0.03a | 11.1 ± 1.71a |
| R2 | 0.36 ± 0.11a | 16.3 ± 2.04a |
| Y15 | 1.45 ± 0.16b | 36.9 ± 4.23b |

The invention claimed is:

1. An RNAi construct comprising a fragment of *Fusarium* chitin synthase gene Chs3b selected from the group consisting of: Chs3b-1 having the nucleotide sequence of SEQ ID NO: 2, Chs3b-2 having the nucleotide sequence of SEQ ID NO: 3, Chs3b-3 having the nucleotide sequence of SEQ ID NO: 4, Chs3b-4 having the nucleotide sequence of SEQ ID NO: 5, and Chs3b-5 having the nucleotide sequence of SEQ ID NO:6.

2. The RNAi construct according to claim 1, which is a plant transformation vector, comprising a constitutive promoter and a terminator.

3. A transfected cell comprising the RNAi construct according to claim 1, wherein the cell is a bacterial cell, an animal cell or a plant cell.

4. A method for producing a plant resistant to *Fusarium* head blight, comprising the steps of transforming the plant with the RNAi construct according to claim 1, and expressing the RNAi construct to form a dsRNA/siRNA or antisense sequence to thereby silence the *Fusarium* chitin synthase Chs3b gene.

5. The method according to claim 4, wherein the plant is selected from the group consisting of wheat, barley, corn, rice, rapeseed and oat.

6. A plant resistant to *Fusarium* head blight produced by the method of claim 4.

7. The plant resistant to *Fusarium* head blight according to claim 6 which is selected from the group consisting of wheat, barley, corn, rice, rapeseed and oat.

8. The RNAi construct according to claim 2, wherein the promoter is a corn Ubi promoter.

9. The RNAi construct according to claim 2, wherein the terminator is a Nos terminator.

10. The RNAi construct transfected cell according to claim 3, wherein the cell is a fungal cell.

* * * * *

SEQUENCE LISTING

<160> NUMBER OF SEQ ID NOS: 28

<210> SEQ ID NO 1
<211> LENGTH: 2718
<212> TYPE: DNA
<213> ORGANISM: Fusarium

<400> SEQUENCE: 1

```
atggcgtaca atggccgtga ccaggagtat ggaggccatg ccctccagga ccttcctgct      60
ggcagtagcc agtaccatct tcccctcaa  gagaatgaag aggagcaggg ccgtggcctt     120
ttgaactcgg gctacgaaca agatcgactc ggcgcccgaa ctcctcccga ccgccctgtc     180
tctgcttaca gtcttactga gtcctatgcc cctggtgctt cgtccgccat gcccggccag     240
ggacctactg gatatggcga cactggtggc agcttcggcc agtttggaaa cctggatgcc     300
aatgctcctt tccctcgccc cgactctgcc tttgatcctg aggacagctg ggttgagcgt     360
cagcagcagc cccagatggg tggtggcggt ggccttggtc gttcaaagac ccgaaagatc     420
aagctggttc agggttcagt cctgagcatt gattacccccg ttcccagtgc catcaagaac     480
gctgttcagc ctcaataccg tgatgccgag agtggcactg aggaattcca caagatgcga     540
tacaccgctg ccacatgtga ccccaacgac ttcaccctca agaatggtta cgatttgcgg     600
cctcgcatgt acaaccgaca cactgagctg cttattgcca ttacatacta taacgaagac     660
aaggttctgc ttgcccgaac cctgcatcac actatgcaga acatccgcga tatcgtcaac     720
ctgaagaagt cgactttctg gaacaagggt ggccctgctt ggcagaagat cgttgtctgc     780
ttggttttcg acggtattga taaggctgac aagaacaccc ttgatgtact tgccaccgta     840
ggtgtttacc aggatggtgt catcaagaag gatgtcgacg gcaaggagac cgttgcccac     900
atcttcgaat acacctccca gctttccgtc accccaacc  agcagctcat ccgacctaca     960
aacgagggtt cccagaacct gccaccagtt cagatgatct tctgtttgaa gcagaagaac    1020
accaagaaga tcaactctca tcgatggttg ttcaacgcct tcggtcgtat cccgaaccct    1080
gaggtgtgta ttctgcttga tgcgggtacc aagcccagtc ccgatcgct  ccttgctctt    1140 tgggagggtt tctacaacga caaggatctt ggtggtgctt gtggtgaaat tcacgccatg    1200
ttgggtaagg gcggcaagaa gctgttcaac cccctcgttg ctgtccagaa cttcgagtac    1260
aagatctcca acattctcga caagcctctt gagtcatctt tcggttacgt tagcgtgttg    1320
cccggtgcct tctctgctta tcgattccgt gcgatcatgg gtcgtcctct ggagcaatat    1380
ttccatggtg atcatacttt gtctaagatg cttggtaaga agggtatcga cggtatgaac    1440
attttcaaga agaacatgtt cttggctgag gatcgtattc tgtgtttcga gctggtcgcc    1500
aaggctggcc agaagtggca tttgtcttat atcaaggctg ccaagggtga aaccgatgtt    1560
```

```
cccgaaggtg ccgctgaatt catcagtcag cgtcgtcgtt ggctcaacgg ttcgttcgct   1620
gccactctgt actcgctgat gcacttcggt cgaatgtaca agtcgggtca taacatcatt   1680
cgcatgttct tccttcacat tcagctcatc tacacgactc tcaacactat gtttgcttgg   1740
ttctctctcg gttcttactg gcttacaaca tccgtcatta tggaccttgt gggtaaacct   1800
aatactacct ctggagttca cgcttggcca ttcggtgaca caggtactcc catcgtcaac   1860
gctctgctcc aatacctcta cctggccttt gttatgctcc agttcattct ggctctgggt   1920
aacagaccca agggttcaaa gtttacttat atcgcttcgt tcatggtctt cggtctcatc   1980
cagggttaca tcctggttct gtccgcttac ctggtcgttc gtgcctttga cacacctgtt   2040
ggagaccaga tctcgtttgc ttcgaccgac gcttttctga acagtttctt cggtggttca   2100
agcgctggtg gtgttatttt ggtcgctctt attaccattt acggattgaa ctttattgcc   2160
tcattcatgt acctcgaccc ttggcacatg ttccactcct tcccttacta cctggttctc   2220
atgtcaactt acatcaacat tctcatggtc tacgcgttca caactggca cgatgtttct   2280
tggggtacca agggttccga caaggctgag gcacttccct ctgcccacgt caccaaggga   2340
gagaagaacg aggttgtcgt cgaggaagtc gagaaggagc aggaggatat tgatagtcag   2400
tttgagcaaa cagtccgccg tgctcttgct cctttcaagg aagaggagga ggtcgagaag   2460
gccgatgtcg aggatggtta caagtctttc cgaactggtc tcgtcgtctg ctggttgttt   2520
ggaaacattc ttctcattgt ttgcatcacc agcaccaact ttgataaacct tggatggggt   2580
gaacctgcca cagaacgaaa ggcgcattac ttccagttcc ttctgtatgc tactgccgtg   2640
ctctcgcttg ttcgtttctt cggttttcttg tggttcctcg gcaggactgg tatcatgtgc   2700
tgtttctcaa gaaattaa                                                2718

<210> SEQ ID NO 2
<211> LENGTH: 569
<212> TYPE: DNA
<213> ORGANISM: Fusarium

<400> SEQUENCE: 2
atggcgtaca atggccgtga ccaggagtat ggaggccatg ccctccagga ccttcctgct     60
ggcagtagcc agtaccatct tcccctcaa gagaatgaag aggagcaggg ccgtggcctt    120
ttgaactcgg gctacgaaca agatcgactc ggcgcccgaa ctcctcccga ccgccctgtc    180
tctgcttaca gtcttactga gtcctatgcc cctggtgctt cgtccgccat gcccggccag    240
ggacctactg gatatggcga cactggtggc agcttcggcc agtttggaaa cctggatgcc    300
aatgctcctt tccctcgccc cgactctgcc tttgatcctg aggacagctg ggttgagcgt    360
cagcagcagc cccagatggg tggtggcggt ggccttggtc gttcaaagac ccgaaagatc    420
aagctggttc agggttcagt cctgagcatt gattaccccg ttcccagtgc catcaagaac    480
gctgttcagc tcaataccg tgatgccgag agtggcactg aggaattcca caagatgcga    540
tacaccgctg ccacatgtga ccccaacga                                      569

<210> SEQ ID NO 3
<211> LENGTH: 587
<212> TYPE: DNA
<213> ORGANISM: Fusarium

<400> SEQUENCE: 3
cttcaccctc aagaatggtt acgatttgcg gcctcgcatg tacaaccgac acactgagct     60
gcttattgcc attacatact ataacgaaga caaggttctg cttgcccgaa ccctgcatca    120
```

```
cactatgcag aacatccgcg atatcgtcaa cctgaagaag tcgactttct ggaacaaggg    180
tggccctgct tggcagaaga tcgttgtctg cttggttttc gacggtattg ataaggctga    240
caagaacacc cttgatgtac ttgccaccgt aggtgtttac caggatggtg tcatcaagaa    300
ggatgtcgac ggcaaggaga ccgttgccca catcttcgaa tacacctccc agctttccgt    360
cacccccaac cagcagctca tccgacctac aaacgagggt tcccagaacc tgccaccagt    420
tcagatgatc ttctgtttga agcagaagaa caccaagaag atcaactctc atcgatggtt    480
gttcaacgcc ttcggtcgta tcccgaaccc tgaggtgtgt attctgcttg atgcgggtac    540
caagcccagt ccccgatcgc tccttgctct ttgggagggt ttctaca                  587

<210> SEQ ID NO 4
<211> LENGTH: 500
<212> TYPE: DNA
<213> ORGANISM: Fusarium

<400> SEQUENCE: 4
tccttgctct ttgggagggt ttctacaacg acaaggatct tggtggtgct tgtggtgaaa    60
ttcacgccat gttgggtaag gcggcaagaa agctgttcaa ccccctcgtt gctgtccaga    120
acttcgagta caagatctcc aacattctcg acaagcctct tgagtcatct ttcggttacg    180
ttagcgtgtt gcccggtgcc ttctctgctt atcgattccg tgcgatcatg ggtcgtcctc    240
tggagcaata tttccatggt gatcatactt tgtctaagat gcttggtaag aagggtatcg    300
acggtatgaa cattttcaag aagaacatgt tcttggctga ggatcgtatt ctgtgtttcg    360
agctggtcgc caaggctggc cagaagtggc atttgtctta tatcaaggct gccaagggtg    420
aaaccgatgt tcccgaaggt gccgctgaat tcatcagtca gcgtcgtcgt tggctcaacg    480
gttcgttcgc tgccactctg                                                500

<210> SEQ ID NO 5
<211> LENGTH: 523
<212> TYPE: DNA
<213> ORGANISM: Fusarium

<400> SEQUENCE: 5
tcgttcgctg ccactctgta ctcgctgatg cacttcggtc gaatgtacaa gtcgggtcat    60
aacatcattc gcatgttctt ccttcacatt cagctcatct acacgactct caacactatg    120
tttgcttggt tctctctcgg ttcttactgg cttacaacat ccgtcattat ggaccttgtg    180
ggtaaaccta atactacctc tggagttcac gcttggccat tcggtgacac aggtactccc    240
atcgtcaacg ctctgctcca atacctctac ctggcctttg ttatgctcca gttcattctg    300
gctctgggta acagacccaa gggttcaaag tttacttata tcgcttcgtt catggtcttc    360
ggtctcatcc agggttacat cctggttctg tccgcttacc tggtcgttcg tgcctttgac    420
acacctgttg gagaccagat ctcgtttgct tcgaccgacg cttttctgaa cagtttcttc    480
ggtggttcaa gcgctggtgg tgttatttg gtcgctctta tta                      523

<210> SEQ ID NO 6
<211> LENGTH: 615
<212> TYPE: DNA
<213> ORGANISM: Fusarium

<400> SEQUENCE: 6
gctggtggtg ttatttggt cgctcttatt accatttacg gattgaactt tattgcctca    60
```

```
ttcatgtacc tcgacccttg cacatgttc cactccttcc cttactacct ggttctcatg    120
tcaacttaca tcaacattct catggtctac gcgttcaaca actggcacga tgtttcttgg    180
ggtaccaagg gttccgacaa ggctgaggca cttccctctg cccacgtcac caagggagag    240
aagaacgagg ttgtcgtcga ggaagtcgag aaggagcagg aggatattga tagtcagttt    300
gagcaaacag tccgccgtgc tcttgctcct ttcaaggaag aggaggaggt cgagaaggcc    360
gatgtcgagg atggttacaa gtcttttccga actggtctcg tcgtctgctg gttgtttgga    420
aacattcttc tcattgtttg catcaccagc accaactttg ataaccttgg atggggtgaa    480
cctgccacag aacgaaaggc gcattacttc cagttccttc tgtatgctac tgccgtgctc    540
tcgcttgttc gtttcttcgg tttcttgtgg ttcctcggca ggactggtat catgtgctgt    600
ttctcaagaa attaa                                                     615

<210> SEQ ID NO 7
<211> LENGTH: 33
<212> TYPE: DNA
<213> ORGANISM: Artificial Sequence
<220> FEATURE:
<223> OTHER INFORMATION: A synthetic oligonucleotide for Chs3bRNAi1s-P1

<400> SEQUENCE: 7
tcccccgggt cttgagggtg aagtcgttgg gat                                 33

<210> SEQ ID NO 8
<211> LENGTH: 38
<212> TYPE: DNA
<213> ORGANISM: Artificial Sequence
<220> FEATURE:
<223> OTHER INFORMATION: A synthetic oligonucleotide for Chs3bRNAi1s-P2

<400> SEQUENCE: 8
ataagaatgc ggccgcccgt gaccaggagt atggaggc                            38

<210> SEQ ID NO 9
<211> LENGTH: 34
<212> TYPE: DNA
<213> ORGANISM: Artificial Sequence
<220> FEATURE:
<223> OTHER INFORMATION: A synthetic oligonucleotide for Chs3bRNAi2s-P1

<400> SEQUENCE: 9
tcccccgggt gtagaaaccc tcccaaagag caag                                34

<210> SEQ ID NO 10
<211> LENGTH: 40
<212> TYPE: DNA
<213> ORGANISM: Artificial Sequence
<220> FEATURE:
<223> OTHER INFORMATION: A synthetic oligonucleotide for Chs3bRNAi2s-P2

<400> SEQUENCE: 10
ataagaatgc ggccgccttc accctcaaga acggttacga                          40

<210> SEQ ID NO 11
<211> LENGTH: 30
<212> TYPE: DNA
<213> ORGANISM: Artificial Sequence
<220> FEATURE:
<223> OTHER INFORMATION: A synthetic oligonucleotide for Chs3bRNAi3s-P1

<400> SEQUENCE: 11
tcccccgggc agagtggcag cgaacgaacc                                     30
```

<210> SEQ ID NO 12
<211> LENGTH: 39
<212> TYPE: DNA
<213> ORGANISM: Artificial Sequence
<220> FEATURE:
<223> OTHER INFORMATION: A synthetic oligonucleotide for Chs3bRNAi3s-P2

<400> SEQUENCE: 12
ataagaatgc ggccgctcct tgctctttgg gagggtttc                        39

<210> SEQ ID NO 13
<211> LENGTH: 39
<212> TYPE: DNA
<213> ORGANISM: Artificial Sequence
<220> FEATURE:
<223> OTHER INFORMATION: A synthetic oligonucleotide for Chs3bRNAi4s-P1

<400> SEQUENCE: 13
tcccccgggt aataagagcg accagaataa caccaccag                        39

<210> SEQ ID NO 14
<211> LENGTH: 46
<212> TYPE: DNA
<213> ORGANISM: Artificial Sequence
<220> FEATURE:
<223> OTHER INFORMATION: A synthetic oligonucleotide for Chs3bRNAi4s-P2

<400> SEQUENCE: 14
ataagaatgc ggccgctcgt tcgctgccac tctgtactcg ctgatg                46

<210> SEQ ID NO 15
<211> LENGTH: 33
<212> TYPE: DNA
<213> ORGANISM: Artificial Sequence
<220> FEATURE:
<223> OTHER INFORMATION: A synthetic oligonucleotide for Chs3bRNAi5s-P1

<400> SEQUENCE: 15
tcccccgggc ctgccgagga accacaagaa acc                              33

<210> SEQ ID NO 16
<211> LENGTH: 43
<212> TYPE: DNA
<213> ORGANISM: Artificial Sequence
<220> FEATURE:
<223> OTHER INFORMATION: A synthetic oligonucleotide for Chs3bRNAi5s-P2

<400> SEQUENCE: 16
ataagaatgc ggccgcgctg gtggtgttat tctggtcgct ctt                   43

<210> SEQ ID NO 17
<211> LENGTH: 21
<212> TYPE: DNA
<213> ORGANISM: Artificial Sequence
<220> FEATURE:
<223> OTHER INFORMATION: A synthetic oligonucleotide sequence

<400> SEQUENCE: 17
atggcgtaca atggccgtga c                                           21

<210> SEQ ID NO 18
<211> LENGTH: 19
<212> TYPE: DNA
<213> ORGANISM: Artificial Sequence
<220> FEATURE:

<223> OTHER INFORMATION: A synthetic oligonucleotide sequence

<400> SEQUENCE: 18
ttaatttctt gagaaacag                                                    19

<210> SEQ ID NO 19
<211> LENGTH: 36
<212> TYPE: DNA
<213> ORGANISM: Artificial Sequence
<220> FEATURE:
<223> OTHER INFORMATION: A synthetic oligonucleotide sequence

<400> SEQUENCE: 19
ataagaatgc ggccgcgctt ggtaaggaaa taatta                                 36

<210> SEQ ID NO 20
<211> LENGTH: 41
<212> TYPE: DNA
<213> ORGANISM: Artificial Sequence
<220> FEATURE:
<223> OTHER INFORMATION: A synthetic oligonucleotide sequence

<400> SEQUENCE: 20
ttccccgcgg ggatcgagct ctcttgaggg tgaagtcgtt g                           41

<210> SEQ ID NO 21
<211> LENGTH: 46
<212> TYPE: DNA
<213> ORGANISM: Artificial Sequence
<220> FEATURE:
<223> OTHER INFORMATION: A synthetic oligonucleotide sequence

<400> SEQUENCE: 21
ttccccgcgg ggatcgagct ctgtagaaac cctcccaaag agcaag                      46

<210> SEQ ID NO 22
<211> LENGTH: 42
<212> TYPE: DNA
<213> ORGANISM: Artificial Sequence
<220> FEATURE:
<223> OTHER INFORMATION: A synthetic oligonucleotide sequence

<400> SEQUENCE: 22
ttccccgcgg ggatcgagct ccagagtggc agcgaacgaa cc                          42

<210> SEQ ID NO 23
<211> LENGTH: 46
<212> TYPE: DNA
<213> ORGANISM: Artificial Sequence
<220> FEATURE:
<223> OTHER INFORMATION: A synthetic oligonucleotide sequence

<400> SEQUENCE: 23
ttccccgcgg ggttcgagct ctaataagag cgaccagaat aacacc                      46

<210> SEQ ID NO 24
<211> LENGTH: 45
<212> TYPE: DNA
<213> ORGANISM: Artificial Sequence
<220> FEATURE:
<223> OTHER INFORMATION: A synthetic oligonucleotide sequence

<400> SEQUENCE: 24
tgctccgcgg cgatcgagct ttaatttctt gagaaacagc acatg                       45

```
<210> SEQ ID NO 25
<211> LENGTH: 23
<212> TYPE: DNA
<213> ORGANISM: Artificial Sequence
<220> FEATURE:
<223> OTHER INFORMATION: A synthetic oligonucleotide sequence

<400> SEQUENCE: 25 gtttctttg tcgatgctca ccc                                            23

<210> SEQ ID NO 26
<211> LENGTH: 21
<212> TYPE: DNA
<213> ORGANISM: Artificial Sequence
<220> FEATURE:
<223> OTHER INFORMATION: A synthetic oligonucleotide sequence

<400> SEQUENCE: 26
ccgactctgc ctttgatcct g                                             21

<210> SEQ ID NO 27
<211> LENGTH: 20
<212> TYPE: DNA
<213> ORGANISM: Artificial Sequence
<220> FEATURE:
<223> OTHER INFORMATION: A synthetic oligonucleotide sequence

<400> SEQUENCE: 27
atcttggtgg tgcttgtggt                                               20

<210> SEQ ID NO 28
<211> LENGTH: 22
<212> TYPE: DNA
<213> ORGANISM: Artificial Sequence
<220> FEATURE:
<223> OTHER INFORMATION: A synthetic oligonucleotide sequence

<400> SEQUENCE: 28
gtcgctctta ttaccattta cg                                            22
```